US012714882B2

(12) United States Patent
Gong

(10) Patent No.: US 12,714,882 B2
(45) Date of Patent: Aug. 25, 2026

(54) NEUTRON CAPTURE THERAPY SYSTEM AND NEUTRON GENERATION PART RECOVERY METHOD THEREFOR

(71) Applicant: NEUBORON THERAPY SYSTEM LTD., Xiamen (CN)

(72) Inventor: Qiu-ping Gong, Xiamen (CN)

(73) Assignee: NEUBORON THERAPY SYSTEM LTD., Xiamen (CN)

( * ) Notice: Subject to any disclaimer, the term of this patent is extended or adjusted under 35 U.S.C. 154(b) by 415 days.

(21) Appl. No.: 18/373,338

(22) Filed: Sep. 27, 2023

(65) Prior Publication Data

US 2024/0017096 A1 Jan. 18, 2024

Related U.S. Application Data

(63) Continuation of application No. PCT/CN2022/084324, filed on Mar. 31, 2022.

(30) Foreign Application Priority Data

Mar. 31, 2021 (CN) ......................... 202110349074.6

(51) Int. Cl.
*A61N 5/10* (2006.01)
*G21K 1/00* (2026.01)
*G21K 5/04* (2006.01)

(52) U.S. Cl.
CPC ......... *A61N 5/1078* (2013.01); *A61N 5/1048* (2013.01); *G21K 1/00* (2013.01);
(Continued)

(58) Field of Classification Search
CPC ................ A61N 5/1078; A61N 5/1048; A61N 2005/1087; A61N 2005/109;
(Continued)

(56) References Cited

U.S. PATENT DOCUMENTS 7,785,098 B1 * 8/2010 Appleby ................ G21K 1/025 264/319
9,421,399 B2 * 8/2016 Shapiro ................ A61B 6/4233
(Continued)

FOREIGN PATENT DOCUMENTS

CN 101521981 A 9/2009
CN 104001270 A 8/2014
(Continued)

OTHER PUBLICATIONS

International Search Report of PCT/CN2022/084324, Jun. 28, 2022.

*Primary Examiner* — David A Vanore
(74) *Attorney, Agent, or Firm* — Troutman Pepper Locke LLP; Tim Tingkang Xia, Esq.

(57) ABSTRACT

A neutron capture therapy system, including an accelerator for generating a charged particle beam, a transmission device for transmitting the charged particle beam, a neutron generation part for generating a neutron beam by reacting with the charged particle beam, a beam shaping body for performing spectrum adjustment on the neutron beam, and a guidance device. The transmission device at least includes a first transmission part and a second transmission part which is detachably connected to the first transmission part, the first transmission part includes a first position L1 and a second position L2, and the guidance device guides the first transmission part and the neutron generation part to move from the first position L1 which the neutron generation part is accommodated in the beam shaping body to the second position L2 which the neutron generation part is separated from the beam shaping body.

18 Claims, 15 Drawing Sheets

(52) U.S. Cl.
CPC ........ *G21K 5/04* (2013.01); *A61N 2005/1087* (2013.01); *A61N 2005/109* (2013.01); *A61N 2005/1094* (2013.01)

(58) Field of Classification Search
CPC ............ A61N 2005/1094; A61N 5/103; A61N 2005/1092; A61N 5/1077; G21K 1/00; G21K 5/04; G21K 1/08; G21K 5/08; G21F 3/00; H05H 3/06; H05H 2277/11
See application file for complete search history.

(56) References Cited

U.S. PATENT DOCUMENTS 11,966,569 B2 * 4/2024 Degen .................... G06V 10/25
2007/0084474 A1 4/2007 Rivard
2010/0166142 A1 * 7/2010 Du ......................... G01N 23/10 378/53
2011/0169616 A1 * 7/2011 Yoder ...................... G01T 3/00 340/10.6
2015/0338525 A1 * 11/2015 Valentino ................. G01T 1/16 250/395
2017/0062086 A1 3/2017 Park, Jr. et al.
2017/0173262 A1 * 6/2017 Veltz ...................... G16H 20/17
2018/0206323 A1 * 7/2018 Kobernik ................ H01P 3/123
2019/0131020 A1 * 5/2019 Wei .......................... G21C 1/02
2020/0134773 A1 * 4/2020 Pinter ................ G01N 21/8806
2020/0246639 A1 * 8/2020 Liu ...................... A61N 5/1078

FOREIGN PATENT DOCUMENTS

CN 104149067 A 11/2014
CN 107532220 A * 1/2018 ........... C13K 13/002
CN 107569778 A * 1/2018
CN 107569779 A * 1/2018
CN 107884425 A * 4/2018 ............. G01N 33/24
CN 207243428 U 4/2018
CN 207264793 U 4/2018
CN 108136200 A 6/2018
CN 109925607 A 6/2019
CN 110849684 A 2/2020
CN 111141763 A * 5/2020 ............. G01N 23/20
CN 111686376 A 9/2020
CN 211410738 U * 9/2020
CN 211675930 U * 10/2020
CN 111905275 A * 11/2020 ............... G21K 5/04
CN 212364841 U 1/2021
CN 113491841 A 10/2021
CN 115137992 A * 10/2022 ........... A61N 5/1048
CN 115137993 A * 10/2022 ........... A61N 5/1048
CN 115137994 A * 10/2022 ............. A61N 5/103
CN 217724360 U * 11/2022 ............. A61N 5/103
CN 217745384 U * 11/2022 ........... A61N 5/1048
CN 217745385 U * 11/2022 ........... A61N 5/1048
JP 2013019692 A 1/2013
JP 2013167489 A 8/2013
JP 2014236913 A 12/2014
JP 2015082376 A 4/2015
JP 2015145882 A 8/2015
JP 2019215294 A 12/2019
JP 2020518352 A 6/2020
KR 20090092713 A 9/2009
RU 2721284 C2 5/2020
RU 2727576 C1 7/2020
RU 2739171 C1 12/2020
TW I757723 3/2022
WO 2021185277 A1 9/2021
WO 2022010795 A1 1/2022
WO WO-2022206883 A1 * 10/2022 ........... A61N 5/1048
WO 2023045904 A1 3/2023

* cited by examiner

NEUTRON CAPTURE THERAPY SYSTEM AND NEUTRON GENERATION PART RECOVERY METHOD THEREFOR

CROSS-REFERENCE TO RELATED PATENT APPLICATION

This application is a continuation application of International Application No. PCT/CN2022/084324, filed on Mar. 31, 2022, which claims priority to Chinese Patent Application No. 202110349074.6, filed on Mar. 31, 2021, the disclosures of which are hereby incorporated by reference.

TECHNICAL FIELD

An aspect of the disclosure relates to a radioactive ray irradiation system, and in particular to a neutron capture therapy system; and another aspect of the disclosure relates to a method for recovering radioactive consumables of a radioactive ray irradiation system, and in particular to a method for recovering a neutron generation part of a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

With the development of atomics, radioactive ray therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radioactive ray therapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example boron neutron capture therapy (BNCT), provides a better cancer treatment choice than traditional radioactive rays, by aggregation of boron-containing drugs in tumor cells in combination with precise neutron beam regulation and control.

In a neutron capture therapy system with an accelerator, a charged particle beam is accelerated by the accelerator, to reach an energy sufficient to overcome Coulomb repulsive forces of atomic nucleus of a neutron generation part in a beam shaping body, and generate a nuclear reaction with the neutron generation part to generate neutrons. Therefore, during generation of the neutrons, the neutron generation part is subjected to irradiation of the accelerated charged particle beam with high-power, and temperature of the neutron generation part increases significantly, thereby affecting service life of the neutron generation part. In order to generate neutrons stably, it is need to recover and maintain an old neutron generation part and replace it by a new neutron generation part, therefore, it is need to periodically replace the neutron generation part. The neutron generation part irradiated by the accelerated charged particle beam with a high-energy-grade holds a large number of radioactive rays inevitably, so that when the neutron generation part is replaced at a short distance, there will be a hidden trouble of radiation safety inevitably without enough protection or isolation measures.

SUMMARY

According to an aspect of the disclosure, there is provided a neutron capture therapy system, including an accelerator configured to generate a charged particle beam, a transmission device configured to transmit the charged particle beam and including at least a first transmission part and a second transmission part, a neutron generation part made of radioactive consumables and configured to generate a neutron beam by reacting with the charged particle beam, a beam shaping body configured to perform spectrum adjustment on the neutron beam, and a guidance device. Here the first transmission part is detachably connected to the second transmission part and includes a first position and a second position, the neutron generation part is arranged at an end of the first transmission part, and the guidance device is capable of guiding the first transmission part to move from the first position to the second position. Here when the first transmission part is located at the first position, the neutron generation part at the end of the first transmission part is accommodated in the beam shaping body and is capable of reacting with the charged particle beam to generate neutrons; and when the first transmission part is located at the second position, the neutron generation part is separated from the beam shaping body, and at this time, each of the first transmission part and the neutron generation part are in a replaceable state.

When the neutron generation part made of radioactive consumables is located in the beam shaping body, a radiation shield in the beam shaping body may shield radioactive rays leaked from the neutron generation part to prevent the radioactive rays from irradiating an operator. When the neutron generation part is separated from the beam shaping body, the neutron generation part is exposed in an operation space, and operation time of the operator may be shortened, and/or an operation distance between the operator and the neutron generation part may be increased, so that radiation leaked from the neutron generation part is prevented from irradiating the operator as much as possible in a process of the neutron generation part moving from the first position to the second position along with the first transmission part. According to the technical solution provided in the aspect of the guidance device may quickly, stably and reliably guide the neutron generation part to be recovered from the first operation position to the radiation shielding device at the second position, and in an operation process of replacing the neutron generation part, the operator has an operation condition of keeping an enough safe distance from the neutron generation part and even completely isolating from the neutron generation part, thereby avoiding excessive radiation damage effectively.

Further, the guidance device may include a first guidance part and a second guidance part, of which guiding directions are different from each other. According to an embodiment of the disclosure, in case that available space in an operation chamber is narrow and limited, the first guidance part of the guidance device guides the first transmission part of the transmission device to move in a first direction along which the transmission device is arranged and enter the second guidance part of the guidance device, to avoid some facilities and obstacles that may exist in the first direction. Such arrangement facilitates miniaturization and compactness of the operation chamber, improves utilization of the space, and reduces occupied area and construction cost.

Further, in a plane where the first guidance part is located parallel to the ground, a projection of a connection line between a first end and a second end of the second guidance part may form a first angle with the first guidance part; and in a plane where the first guidance part is located perpendicular to the ground, a projection of the connection line between the first end and the second end of the second guidance part may form a second angle with the first guidance part.

Further, the second guidance part may include at least two segments of guide rails, one of which is a fixed rail detachably connected to the first guidance part, and the other of which is movable rail rotatably connected to the fixed rail.

Further, the movable rail may be connected to the fixed rail through a hinge structure and may have two positions, and when the movable rail is located at a first position, the movable rail and the fixed rail keep a normal guidance state together; and when the movable rail is stressed and located at a second position, the movable rail moves at a certain angle relative to the fixed rail, and may automatically return to the first position.

Further, 90% (weight percentage) or more of materials of the guidance device may be composed of at least one of C, H, O, N, Si, Al, Mg, Li, B, Mn, Cu, Zn, S, Ca, or Ti.

Further, the first guidance part may be made of an aluminum alloy, a magnesium-aluminum alloy, a carbon fiber composite material, a glass fiber composite material, or a combination thereof.

Further, the second guidance part may select materials the same as the first guidance part, or may select materials different from the first guidance part, such as stainless steel and a ferrous material.

Further, a surface of the second guidance part may be coated with an anti-radiation film, or a removable anti-radiation protective cover may be added to the surface of the second guidance part.

Further, a shaped surface of the anti-radiation protective cover may be fitted with a cross-sectional shape of the second guidance part.

According to a second aspect of the disclosure, there is provided a neutron capture therapy system, including an accelerator configured to generate a charged particle beam, a transmission device configured to transmit the charged particle beam and including at least a first transmission part and a second transmission part, a neutron generation part configured to generate a neutron beam by reacting with the charged particle beam, a beam shaping body configured to perform spectrum adjustment on the neutron beam, and a guidance device. Here the first transmission part is detachably connected to the second transmission part, the neutron generation part is arranged on the first transmission part. The neutron capture therapy system further includes a movable radiation shielding device configured to accommodate the first transmission part and the neutron generation part guided by the guidance device, and the radiation shielding device recovers the first transmission part moving along the guidance device and the neutron generation part at an end thereof together.

Further, the guidance device may include a first guidance part and a second guidance part, of which guiding directions are different from each other.

Further, the guidance device may further include a third guidance part which is fixedly accommodated in the movable radiation shielding device.

Further, the second guidance part is detachably connected to the third guidance part, or the second guidance part may be flexibly aligned with and connected to the third guidance part, to conveniently guide the first transmission part of the transmission device into the radiation shielding device.

Further, the radiation shielding device may be made of a radiation shielding material and may include an openable member, the radiation shielding device forms an accommodation opening when the openable member is opened, the first transmission part of the transmission device enters the radiation shielding device from the accommodation opening; and the radiation shielding device forms a closed shielding space when the openable member is closed, to prevent radiation leakage of the neutron generation part.

Further, the movable radiation shielding device may further include a buffer device capable of generating elastic deformation after the first transmission part is in contact with the buffer device, generating elastic deformation and applying an opposite acting force in a movement direction of the first transmission part, so that the first transmission part is safely stopped in the radiation shielding device, to avoid damage to at least the first transmission part or the radiation shielding device. Furthermore, the neutron capture therapy system may include a positioning system enabling the radiation shielding device to move to a preset position, so as to be docked with the guidance device. The positioning system may mark the position in advance according to means such as structural positioning, three-dimensional (3D) algorithm positioning, or the like, so that the radiation shielding device may move to an ideal position aligned with the guidance device, thus the first transmission part and the neutron generation part at the end thereof may be reliably recovered to the radiation shielding device after moving to a tail end of the guidance device.

Further, the movable radiation shielding device may further include a positioning system enabling the radiation shielding device to move to a preset position, so that the second guidance part is docked with the third guidance part.

Further, the neutron generation part may enter the accommodation opening of the movable radiation shielding device along the guidance device, later than the first transmission part, and the openable member is closed after the neutron generation part completely enters the movable radiation shielding device.

Further, after the openable member of the movable radiation shielding device is closed, an internal vacuumized environment or inert gas inflation may be implemented, while physical isolation from external air is implemented.

Further, the neutron capture therapy system may further include a control part capable of implementing opening and closing of the openable member of the movable radiation shielding device through remote control via wired or wireless connection.

According to a third aspect of the disclosure, there is provided a neutron capture therapy system, including an accelerator configured to generate a charged particle beam, a transmission device configured to transmit the charged particle beam and including at least a first transmission part and a second transmission part, a neutron generation part configured to generate a neutron beam by reacting with the charged particle beam, a beam shaping body configured to perform spectrum adjustment on the neutron beam, and a guidance device. Here the first transmission part is detachably connected to the second transmission part and includes a first position and a second position, the neutron generation part is arranged on the first transmission part, and the guidance device is capable of guiding the first transmission part to move from the first position to the second position. Here when the first transmission part is located at the first position, the neutron generation part is accommodated in the beam shaping body and is capable of reacting with the charged particle beam to generate neutrons; and when the first transmission part is located at the second position, the neutron generation part is separated from the beam shaping body. The neutron capture therapy system further includes a driving device providing power to enable the first transmission part to be separated from the beam shaping body, move out of the first position and move along the guidance device.

Further, the neutron capture therapy system may further include a support device stably supporting the first transmission part in a direction along which the transmission device is arranged.

Further, the guidance device may include a first guidance part and a second guidance part, of which guiding directions are different from each other.

Further, the driving device may include a driving frame carrying the first transmission part and the neutron generation part, and a power structure providing a driving force.

Further, the neutron capture therapy system may further include a control part which may implement controlling the power structure of the driving device through remote control via wired or wireless connection, to provide power for movement of the first transmission part and the neutron generation part between the first position and the second position.

Further, the driving frame of the driving device may include at least one set of roller structures.

Further, the driving frame of the driving device may include at least two sets of roller structures, and rolling directions of the two sets of rollers are different.

Further, rolling planes of the two sets of rollers of the driving frame are different and perpendicular to each other.

Further, the at least two sets of roller structures of the driving frame are combined with concave and/or convex sliding rails of the guidance device, to implement transmission movement, and rolling transmission may be implemented by selecting a structure where one or two sets of rollers are matched with the concave and/or convex sliding rails.

Furthermore, the neutron capture therapy system may further include a cooling device configured to cool the neutron generation part and including a cooling pipeline, when the first transmission part is located at the first position, the cooling pipeline is in an on state, and the cooling device performs cooling operation; and when the first transmission part is located at the second position, the cooling pipeline is in an off state, the cooling device cannot perform normal operation, and the cooling device and the first transmission part are recovered and replaced together.

Further, the neutron capture therapy system may further include a detection device including a detection circuit, and when the first transmission part is located at the first position, the detection device is in an on state to perform detection operation; and when the first transmission part is located at the second position, the detection circuit is in an off state and cannot perform normal operation, and the detection device is recovered and replaced together with the cooling device, the neutron generation part and the first transmission part. The "detection device" described here may be a charged particle sensor, or may be a device adapted to be installed at the first transmission part, such as a vacuum pressure sensor, and/or a neutron detector, or the like.

According to a fourth aspect of the disclosure, there is provided a method for recovering the neutron generation part of the neutron capture therapy system as described above, the neutron capture therapy system further includes an auxiliary pipeline connected to the neutron generation part or the first transmission part, the method for recovering the neutron generation part includes the following operations. The first transmission part and the second transmission part are split apart. The auxiliary pipeline is disconnected from the neutron generation part. A first power is applied to the first transmission part arranged with the neutron generation part, to separate the first transmission part from the beam shaping body along the guidance device and from the first position. A second power is applied to the first transmission part arranged with the neutron generation part, to move the first transmission part along the guidance device again, until to a recovery position.

Further, the neutron capture therapy system may further include a shielding facility provided with an opening, and the first transmission part passes through the opening in a state where the shielding facility is kept closed.

Furthermore, the method for recovering the neutron generation part may be carried out through the opening in the state where the shielding facility is kept closed.

Furthermore, the shielding facility may be provided with an auxiliary door, the auxiliary door at least partially shields the opening of the shielding facility and has an opening matched with contours of the first transmission part, the guidance device and the auxiliary pipeline arranged at the opening of the shielding facility when the auxiliary door is closed, and the method for recovering the neutron generation part may be carried out through the opening in a state where the shielding facility is kept closed and the auxiliary door is kept open.

Furthermore, the neutron capture therapy system may further include a radiation shielding device configured to accommodate the neutron generation part after recovery, and a first space and a second space separated by the shielding facility, an anti-radiation protective cover is arranged on the guidance device, the neutron generation part is located in the first space, the second transmission part is located in the second space, and the method for recovering the neutron generation part may further include the following operations. Before applying the first power to the first transmission part arranged with the neutron generation part, the radiation shielding device is moved to the second space and the radiation shielding device is fixed at a preset position, the openable member of the radiation shielding device is opened, and the anti-radiation protective cover on the guidance device is removed. After applying the second power to the first transmission part arranged with the neutron generation part, the first transmission part is moved into the radiation shielding device along the guidance device, the openable member of the radiation shielding device is closed, the anti-radiation protective cover is covered on the guidance device, and the radiation shielding device is pushed out of the second space.

According to a fifth aspect of the disclosure, there is provided a method for recovering the neutron generation part of the neutron capture therapy system as described above, the neutron capture therapy system further includes a shielding facility keeping closed during recovery operation and provided with an opening, and the method for recovering the neutron generation part includes the following operations. A cooling pipeline connected to the neutron generation part is disconnected through the opening of the shielding facility. A first power is applied to the first transmission part arranged with the neutron generation part, to separate the first transmission part from the beam shaping body along the guidance device and from the first position, and move the first transmission part to a position close to the opening of the shielding facility. A second power is applied to the first transmission part arranged with the neutron generation part, to move the first transmission part along the guidance device again, until to a recovery position. Further, the method for recovering the neutron generation part may further include the following operations. A detection circuit of a detection device and other connection lines are cut off while the cooling pipeline is cut off. When the neutron generation part is separated from the beam shaping body, exposure of the neutron generation part may bring large radiation, the shielding facility is kept closed during recovery, and the operator performs replacement operation of the neutron generation part through the opening in the shielding facility, so that radiation leakage of operation environment is greatly reduced, and operation safety is improved.

According to a sixth aspect of the disclosure, there is provided a method for recovering the neutron generation part of the neutron capture therapy system as described above, including the following operations. A shielding facility is kept closed during recovery operation, and the shielding facility is provided with an auxiliary door which is kept in a closing state during system operation. When the system stops and the neutron generation part needs to be replaced, the auxiliary door is opened, a cooling pipeline connected to the neutron generation part is disconnected through an opening of the auxiliary door. A first power is applied to the first transmission part arranged with the neutron generation part, to separate the first transmission part from the beam shaping body along the guidance device and from the first position, and move the first transmission part to a position close to the opening of the shielding facility. A second power is applied to the first transmission part arranged with the neutron generation part, to move the first transmission part along the guidance device again, until the first transmission part enters a recovery position in a radiation shielding device, and the auxiliary door is closed. Further, shape of the opening in the auxiliary door is usually fitted with shapes of the first transmission part, the guidance device and mating pipeline structures, a vacuum valve, or the like arranged at the opening, and the shape includes, but is not limited to, oval shape, rhombus shape, square shape, even an irregular shape, or the like.

In the embodiment of the disclosure, time for the operator to be exposed in an environment of a strong radiation object in a process of replacing radioactive consumables is shortened, and a relatively safe operation distance is provided for the operator and the neutron generation part, so that in an operation process of replacing the radioactive consumables, the operator may have an operation condition of keeping an enough safe distance from the radioactive consumables and even completely isolating from the radioactive consumables, so that contact between the operator and radioactive rays is reduced, and a hidden trouble of radiation safety is reduced. Furthermore, in the embodiment of the disclosure, the neutron capture therapy system belonging to a radioactive ray irradiation system is compact in structure and convenient in installation, and in a condition where operation space is limited, actual space and place are efficiently utilized, occupied area and construction cost are reduced, thus a reliable, stable and safe recovery solution is provided for the neutron generation part.

Further areas of applicability will become apparent from the description provided herein. It should be understood that the description and specific examples are intended for purposes of illustration only and are not intended to limit the scope of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Figure 1:
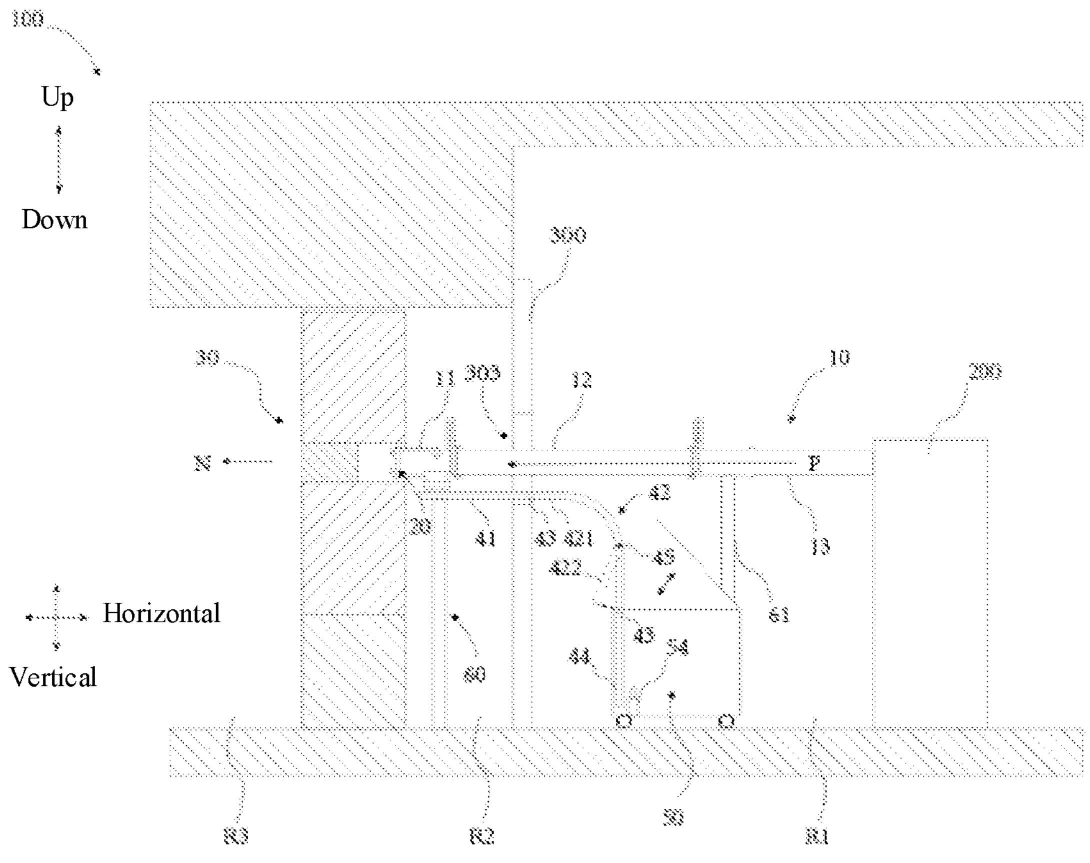
FIG. 1 is a schematic plan view of a neutron capture therapy system according to an embodiment of the disclosure.

Application of neutron capture therapy as an effective means for cancer treatment gradually increases in recent years, in which boron neutron capture therapy (BNCT) is most commonly seen, and neutrons supplied to BNCT may be supplied by a nuclear reactor or an accelerator. Embodiments of the disclosure use an accelerator BNCT as an example, and basic components of the accelerator BNCT usually includes an accelerator configured to accelerate charged particles (such as protons, deuterium cores, or the like), a neutron generation part made of radioactive consumables, a thermal removal system, and a beam shaping body. Here the accelerated charged particles act with the neutron generation part made of metal to generate neutrons, and an appropriate nuclear reaction may be selected according to characteristics such as a desired neutron yield and energy, available energies of the accelerated charged particles, a current, physical and chemical properties of the neutron generation part made of metal, or the like. Nuclear reactions as commonly discussed include $^{7}$Li(p, n) $^{7}$Be and $^{9}$Be(p, n) $^{9}$B, both of which are endothermic reactions and have energy thresholds of 1.881 MeV and 2.055 MeV respectively. An ideal neutron source for BNCT is an epithermal neutron at a keV energy level, theoretically, when protons with energies slightly higher than the threshold are used to bombard the neutron generation part made of metallic lithium, neutrons with relatively low energies may be generated for clinical application without too much retarding treatment. However, proton action sections of two neutron generation parts made of metallic lithium (Li) and beryllium (Be) with the threshold energy are not high, therefore protons with higher energies are usually selected to initiate a nuclear reaction, to generate a large enough neutron flux.

An ideal neutron generation part made of radioactive consumables should have a high neutron yield, the generated neutron energy distribution is close to an epithermal neutron energy region (it will be described in detail below), there is not too much strong penetrating radiation, and there are characteristics such as safe, cheap, easy to operate, resistant to high temperature, or the like. However, nuclear reactions that meet the needs may not be found actually, and the neutron generation part made of metal Li is used in the embodiments of the disclosure. However, it is well known by those skilled in the art that the neutron generation part may also be made of another metallic material other than metallic materials as mentioned above.

Requirements of the thermal removal system vary depending on the selected nuclear reaction. For example, requirements of the thermal removal system are higher in $^{7}$Li(p, n) $^{7}$Be than in $^{9}$Be(p, n) $^{9}$B, due to poor melting point and thermal conductivity of the neutron generation unit made of metal (metal Li). $^{7}$Li(p, n) $^{7}$Be nuclear reaction is used in the embodiments of the disclosure. It may be known therefrom that temperature of the neutron generation part irradiated by an accelerated charged particle beam with a high energy level inevitably increases greatly, thereby affecting service life of the neutron generation part.

Therefore, the neutron capture therapy system belonging to a radioactive ray irradiation system inevitably has a problem of replacing the neutron generation part made of radioactive consumables. In order to solve the problem while contact between the operator and radioactive rays is reduced as much as possible, embodiments of the disclosure provide a neutron capture therapy system, which may stably and reliably recover the neutron generation part, have a limited operation space in a direction of the transmission device and a vertical direction of the neutron generation part, utilize the space effectively, avoid interference and obstruction of operation spaces at the same horizontal height in the direction of the transmission device, regardless of acceleration devices for protons in the transmission device, reduce configuration of the operation space, and reduce occupied area and construction cost as a whole.

In order to replace the neutron generation part made of radioactive consumables while contact between the operator and radioactive rays is reduced as much as possible, embodiments of the disclosure provide a neutron capture therapy system.

Because main radiation to the operator comes from radioactive rays generated by a nuclear reaction occurred after the charged particle beam is irradiated to the neutron generation part made of radioactive consumables, the embodiments of the disclosure are intended to describe disassembling the neutron generation part which reaches the service life and is needed to be recovered after occurrence of the nuclear reaction, and do not relate to installation of a new neutron generation part. Furthermore, orientation words such as upper, lower, horizontal, vertical, or the like mentioned in the embodiments of the disclosure are used to facilitate descriptions and describe positional relationships between components according to illustrated directions, and are not intended to limit substantial absolute directions thereof.

Implementations of the neutron capture therapy system are described below with reference to the drawings.

Figure 2:
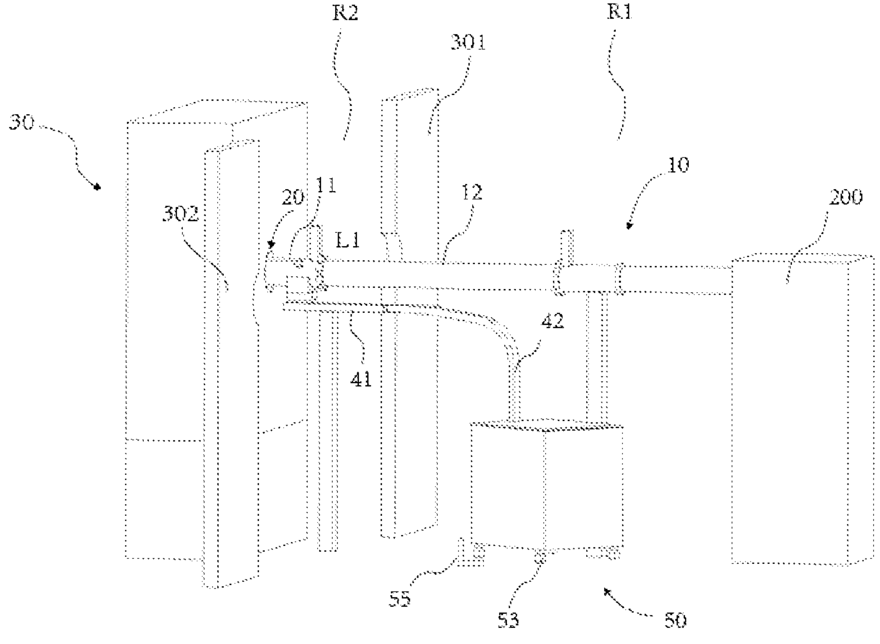
FIG. 2 is a schematic perspective view of a neutron capture therapy system according to an embodiment of the disclosure, showing a first transmission part of a transmission device at a first position and a radiation shielding device in a closed state.

FIG. 1 and FIG. 2 are schematic plan view and schematic perspective view of a neutron capture therapy system according to an embodiment of the disclosure, respectively. As shown in FIG. 1 and FIG. 2, the neutron capture therapy system 100 includes a transmission device 10, a neutron generation part 20 containing radioactive consumables, a beam shaping body 30, a guidance device 40, a radiation shielding device and a support device 60. Here the neutron capture therapy system 100 includes at least a first space R1 and a second space R2, and the first space R1 includes an accelerator 200 configured to generate a charged particle beam P, a part of the transmission device 10 configured to transmit the charged particle beam P, a support device configured to support the transmission device, a detection device, or the like. A transmission direction of the charged particle beam P is consistent with an arrangement direction of the transmission device 10, and the transmission device 10 penetrates the first space R1 and the second space R2. The second space R2 is a core reaction space of the whole system, has a relatively large radiation amount, and is physically separated from the first space R1 through a shielding facility 300, so that radiation amount in the first space R1 is within a relatively safe and controllable range. The shielding facility 300 includes at least a shielding door 301 and/or 302, and further includes at least one opening 303 to allow the transmission device 10 to pass therethrough when the shielding facility 300 is in a closed state. In the illustrated embodiment, interior of the transmission device 10 is in a vacuum state and includes at least a first transmission part 11 and a second transmission part 12 which are detachably connected to each other. Shape of each of the first transmission part and the second transmission part is a hollow tubular shape, and cross-sectional shape of each of the first transmission part and the second transmission part includes, but is not limited to, circular shape, oval shape, diamond shape, square shape, irregular shape, or the like. Shape of at least one opening of the shielding facility 300 may be fitted with shape of the transmission part passing through the opening, including but not limited to circular shape, oval shape, diamond shape, square shape, irregular shape, or the like. In a process of replacing radioactive consumables and splitting the transmission device, each of the first transmission part and the second transmission part of the transmission device may maintain a vacuum state. The second space R2 includes the first transmission part 11 of the transmission device 10, the neutron generation part 20 arranged at an end portion of the transmission device 10 and reacting with the charged particle beam P to generate a neutron beam N, and the beam shaping body 30 configured to perform spectrum adjustment on the neutron beam N. The transmission device 10 transmits charged particles P accelerated by the accelerator 200 from the first space R1 to the neutron generation part 20 in the second space R2. The accelerator 200 accelerates the charged particles P to an energy sufficient to overcome an atomic nuclear force of the target, and produces $^{7}$Li(p, n) $^{7}$Be nuclear reaction with the neutron generation part 20 to generate neutrons which form the neutron beam N emitted from a beam outlet. The beam shaping body 30 is usually large in volume and is not suitable for movement, and is fixedly arranged inside a wall body in an embedded manner. The beam shaping body 30 includes a retarder, a thermal neutron absorber, a radiation shield, or the like (not shown in the drawings). Main material selected by the retarder is usually aluminum fluoride, and optionally, a mixed material of one or more of lithium fluoride, aluminum, lead fluoride, aluminum oxide, calcium fluoride, or magnesium fluoride. Some of these materials have high brittleness, and thus need high level of processing and installation processes. They slow down neutrons generated by the neutron generation part 20 to the epithermal neutron energy zone, and deviated neutrons are guided back to the retarder by a reflector to improve intensity of an epithermal neutron beam. The thermal neutron absorber absorbs thermal neutrons, to avoid unnecessary damage to normal tissues at shallow layers due to excessive dose during treatment. The radiation shield is configured to shield leaked neutrons and photons to reduce dose of normal tissues at non-irradiation regions. The neutron capture therapy system 100 further includes a third space R3 as an irradiation chamber, a neutron beam meeting a condition may be emitted from the beam outlet and enter the irradiation chamber for the usage.

FIG. 2 shows a state of opening the shielding facility 300 between the first space R1 and the second space R2, and when the shielding door 301 and/or the shielding door 302 are opened, the first space R1 is communicated with the second space R2. With reference to FIG. 1, the neutron capture therapy system 100 includes a support device 60 and/or 61 configured to stably support the transmission device 10 in a direction along which the transmission device is arranged. The support device 60 is arranged at a lower portion of the first transmission part 11, an end of the first transmission part 11 arranged with the neutron generation part 10 is accommodated in the beam shaping body 30, the first transmission part 11 is located at a first position L1. In an alternative embodiment, the support device 60 may also be arranged at different orientations such as upper and side portions of the first transmission part 11, or the like, to support it.

Figure 4:
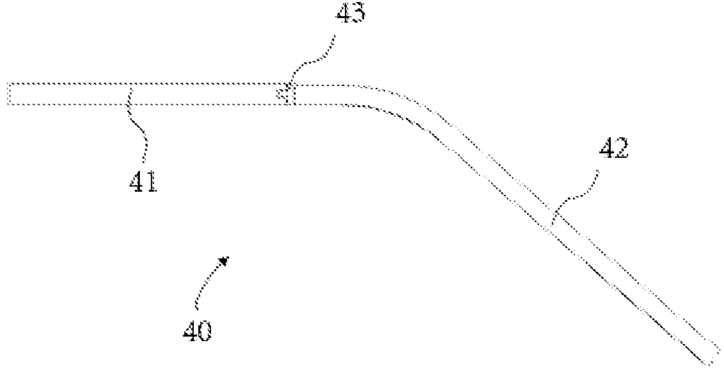
FIG. 4 is a schematic top view of a guidance device of a neutron capture therapy system according to the embodiment of FIG. 1.

With reference to FIG. 1 and FIG. 2, the guidance device 40 is arranged between the support device 60 and the first transmission part 11 (referring to FIG. 4), the neutron capture therapy system 100 further includes a driving device 70 (referring to FIG. 7), the guidance device 40 may include a first rail (a first guidance part) 41 and a second rail (a second guidance part) 42. The first rail 41 substantially extends in a first direction along which the transmission device is arranged, and the first direction is opposite or identical to a movement direction of the charged particle beam P. A first end of the second rail 42 is connected to the first rail 41 through a connection part 43, a second end of the second rail 42 extends in a second direction which is different from the first direction, that is, the guidance device 40 has at least two guiding directions. Guiding directions of the second rail 42 and the first rail 41 are different from each other, which facilitates application of such arrangement in a compact building. With reference to FIG. 4, in an embodiment, in a plane where the first rail is located parallel to the ground, a projection of a connection line between the first end and the second end of the second rail 42 forms a first angle with the first rail 41, for example, the first angle ranges from 10° to 150°, or 30° to 90°; and in a plane where the first rail is located perpendicular to the ground, a projection of the connection line between the first end and the second end of the second rail 42 forms a second angle with the first rail 41. Extension direction of the second rail 42 may avoid other structures, such as the second transmission part 12, and/or the support device 61 of the third transmission part 13, or a beam splitting device, or the like; and in case that the first space R1 has limited operation space in a horizontal direction along which the transmission device 10 is arranged and a vertical direction perpendicular to the ground, a limited operable space is efficiently utilized. In an alternative embodiment, the second rail 42 may also be located in a plane where the first rail 41 is located perpendicular to the ground. The first rail 41 and the second rail 42 are detachably connected to each other through the connection part 43, or there may be a structure where the first rail 41 and the second rail 42 are integrally formed with each other. When the first rail 41 and the second rail 42 form a detachable connection structure, the connection part 43 may be a connection rod, a locking buckle, a concave & convex buckle, or another structure, which may firmly clamp the first rail 41 to the second rail 42, and enable the first transmission part 11 to smoothly slide from the first rail 41 to the second rail 42. An extension length of the first rail 41 limits a certain safety distance, allowing the operator to maintain beyond the safety distance to perform operations such as splitting, debugging, or the like. The second rail 42 is at least partially located in the first space R1, and further the second rail 42 may further include at least two segments of rails 421 and 422. Here an end of the rail 421 is fixedly connected to the first rail 41 through the connection part 43, and the rail 422 is hinged to another end of the rail 421 through a hinge structure 45 and has two positions. The first position is a position where a normal guidance state is kept with the fixed rail 421. The second position is a buffer position where an angle may be formed relative to the first position after subjected to a force during transmission. The rail 422 may automatically rotate and return to the first position. These flexible rail segments improve flexibility and agility of the whole transmission device, and protect the whole system and devices from rigid damage during transmission operations, and are good for subsequent alignment operations. A downward-extending end of the second rail 42 faces the radiation shielding device 50 below it, and the second rail 42 may not be connected to the radiation shielding device, or may at least partially keep connected to the radiation shielding device, and further, the movable rail 422 of the second rail 42 is rotatably aligned with the radiation shielding device. Neutrons are generated in the beam shaping body 30, materials around the beam shaping body 30 are activated most seriously, and the guidance device is partially arranged in the core reaction space R2 with a relatively large radiation amount, therefore material of the guidance device should also be selected carefully. In order to avoid too fast deterioration caused by serious activation, elements having small sections acting with neutrons or short half-life periods (less than 1 year) of radioactive isotopes generated after it is activated by neutrons are usually selected to form the guidance device. For example, 90% (weight percentage) or more of materials of a portion, subjected to large radiation, of the guidance device are composed of at least one of C, H, O, N, Si, Al, Mg, Li, B, Mn, Cu, Zn, S, Ca, or Ti. In the embodiment, When the guidance material selects an aluminum alloy, the aluminum has a short half-life period of 2.2 minutes after it is activated by neutrons; however, element such as iron, cobalt, nickel, or the like contained in a traditional steel material has a long half-life period after it is activated by neutrons, for example, the half-life period of cobalt 60 is 5.27 years. Usage of the aluminum alloy significantly reduces radioactivity derived from neutron activation within a limited period of time, which is more good to disassemble devices in future, in addition to reasonably suppressing dose caused by secondary radiation. The material of the guidance device may further be an aluminum-magnesium alloy, or may be a carbon fiber composite material, a glass fiber composite material, or a combination thereof. The radiation shielding device 50 includes an openable shielding plate 51, an accommodation opening 52 formed by opening the openable shielding plate 51, a movement member 53 and a buffer device 54 inside the movement member 53. The radiation shielding device 50 is made of a radiation shielding material, including, but not limited to, a radiation shield made of lead (Pb), or the like. A wheel-type movement member 53 is arranged at bottom of the radiation shielding device 50, and the openable shielding plate 51 made of a shielding material is covered at top of the radiation shielding device 50, as an openable member. Opening and closing of the openable shielding plate include, but are not limited to, rotation, sliding, or other opening manners. When replacement operation of the neutron generation part is performed, the operator controls the radiation shielding device 50 to move from an external space into the first space R1, to be located at a preset position and docked with a lower end of the second rail 42. In the embodiment, a positioning member 55 is further arranged at the ground, and may stop and position the radiation shielding device 50. In an alternative embodiment, the movement member may be a pre-laid rail or trolley, or the like, and the positioning member may be one or more markers, stop blocks, recessed structures, or the like; the driving device may be a hook, a rope or a cylinder, a linear motor, a chain transmission structure, or the like, which is controlled at a certain spaced distance, and may also be controlled by a wired signal or a wireless signal; and the radiation shielding device 50 includes, but is not limited to, a cube, a sphere, or the like.

Figure 3:
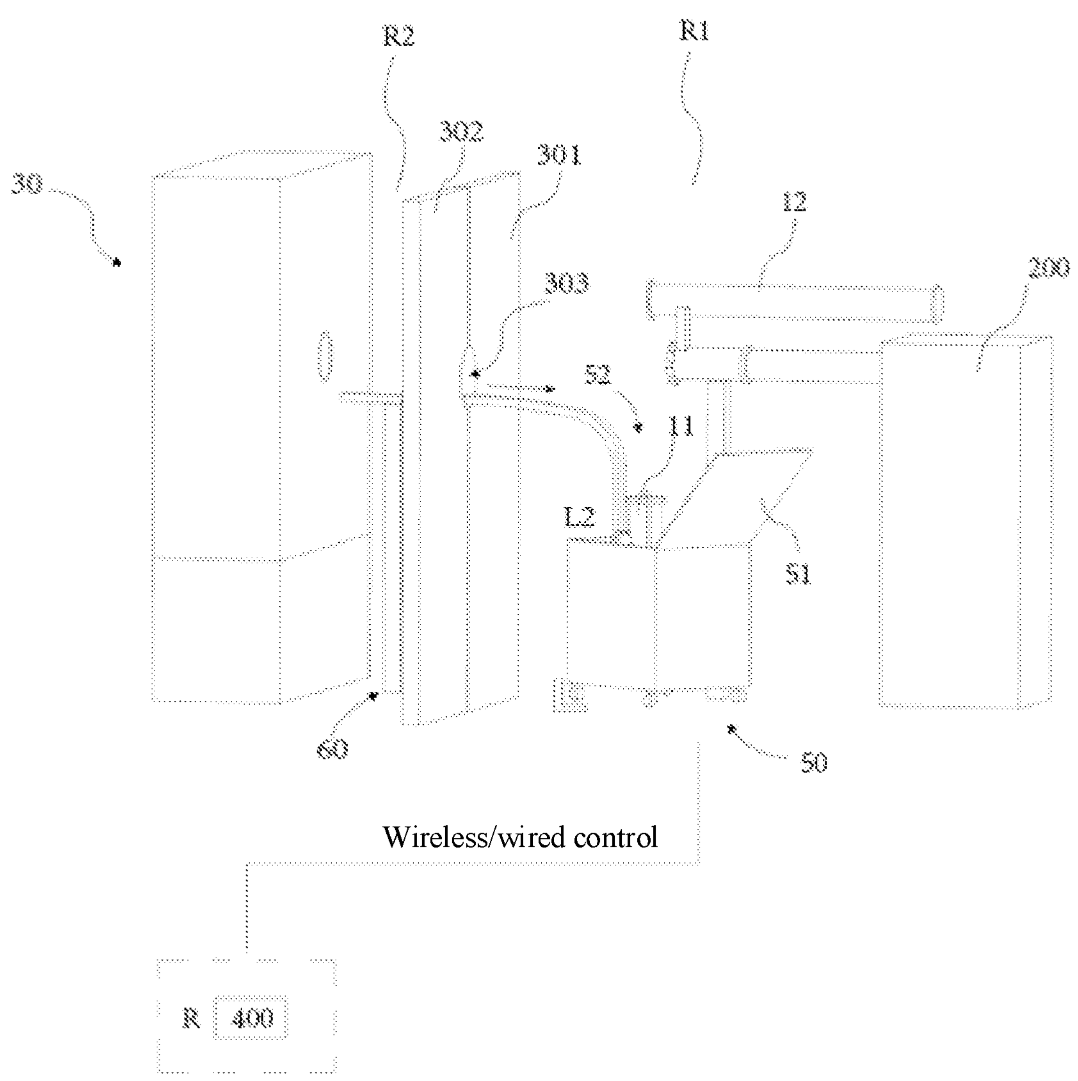
FIG. 3 is a schematic perspective view of a neutron capture therapy system according to an embodiment of the disclosure, showing a first transmission part of a transmission device at a second position and a radiation shielding device in an open state.

The embodiment of FIG. 3 shows a state where replacement operation is performed on the first transmission part 11 with the neutron generation part 20 at an end thereof, the shielding facility 300 is opened, the shielding door 301 and/or the shielding door 302 are opened, and at this time, the first space R1 is communicated with the second space R2. The operator manually or automatically opens the openable shielding plate 51 of the radiation shielding device 50, checks connection and position conditions of the first rail 41, the second rail 42 and the radiation shielding device 50, and performs the replacement operation. With reference to FIG. 1, the transmission device 10 further includes a third transmission part 13, the first transmission part 11 and the second transmission part 12 are split apart, the second transmission part 12 and the third transmission part 13 are split apart, and an overall length of the transmission device 10 is changed by moving the second transmission part 12 out, so that an avoidance space is left, to enable the first transmission part 11 with the neutron generation part 20 at the end thereof to move out along the rail. In splitting processes, the third transmission part may also maintain a vacuum state. In an alternative embodiment, the second transmission part 12 may be fixedly connected to an end of the third transmission part 13, and may be designed as a structure such as a corrugated pipe or a telescopic pipe (not shown) to leave space for the replacement operation. Power from the driving device 70 (referring to FIG. 7) separates the first transmission part 11 with the neutron generation part 20 at the end thereof from the beam shaping body 30, the first transmission section 11 passes through the opening formed by opening the shielding door 301 and the shielding door 302 on the first rail 41 and in a direction along which the transmission device 10, and thus moves to the second rail 42. Under action of gravity or power of the rail, the first transmission part 11 continues to move along the direction of the second rail 42, so that the first transmission part 11 enters the accommodation opening 52 formed by opening the openable shielding plate 51, and at this time, the first transmission part 11 is located at a second position L2. Interior of the radiation shielding device 50 includes at least one buffer device 54 which may buffer the first transmission part 11 and the neutron generation part 20 sliding down. After the first transmission part 11 reaches cavity of the radiation shielding device 50 to be in contact with the buffer device 54, the buffer device generates elastic deformation, so that the first transmission part 11 and the neutron generation part 20 are statically accommodated in the radiation shielding device 50, and the first transmission part and the neutron generation part are prevented from being damaged due to their rapid collision with the radiation shielding device. In an alternative embodiment, when the second rail 42 of the neutron capture therapy system 100 has a short length, a third rail 44 may also be included, an end of the third rail 44 may also be connected to the second rail 42 through the connection part 43, and another end of the third rail 44 is installed inside the radiation shielding device 50. In a solution, the second rail 42 is hinged with a flexibly rotatable rail 422 structure, which facilitates linkage and alignment with the third rail 44 inside the radiation shielding device without rigid connection with the connection part 43, thereby saving installation operations. A buffer cylinder 54 is arranged close to bottom of the third rail 44, and may generate deformation in movement directions of the first transmission part 11 and the neutron generation part 20 to apply opposite acting force, so as to stop and protect the first transmission part 11 and the radiation shielding device 50, and under action of the buffer cylinder 54, the first transmission part 11 and the neutron generation part 20 are safely stopped in the radiation shielding device 50. In an alternative embodiment, the buffer device may also be a different mechanical buffer structure, such as a spring or the like, or may be made of an elastic material, such as a rubber pad, an air bag, or the like. The segments of the first transmission part 11 and the neutron generation part 20 entering the radiation shielding device 50 are sides opposite to the neutron generation part 20 containing radioactive consumables, that is, when recovery operation is completed, the neutron generation part 20 containing radioactive consumables is closer to the accommodation opening 52 of the radiation shielding device 50 and stays at a distal end of the buffer device. Design of such recovery direction focuses on improvement of cyclic utilization rate of the neutron generation part 20 containing radioactive consumables. The neutron generation part 20 located in the beam shaping body 30 is made of relatively active metallic lithium (Li) and/or beryllium (Be), and a coating film of the neutron generation part 20 has thickness of about 100 microns and is relatively easily damaged after it is impacted. Therefore, a recovery direction along which the neutron generation part 20 is the last one to enter the accommodation opening and stays at the distal end of the buffer device is safer than other recovery directions, and the neutron generation part is not easily damaged, greatly improving reuse rate of the neutron generation part containing radioactive consumables and avoiding unnecessary radiation leakage after collision. Furthermore, direction of the neutron generation part 20 is unnecessary to be switched, a tedious and complex direction switching structure or the like are removed, more space is saved, and radiation leakage caused by fault of the switching structure or the like is also avoided. The interior of the radiation shielding device 50 may also implement a vacuumized environment or may be filled with an inert gas, to implement a function of physical isolation from external air, thereby improving safety and reliability of transporting and storing the first transmission part 11 and the neutron generation part 20 or other elements which are easy to have high reactivity.

Figure 5:
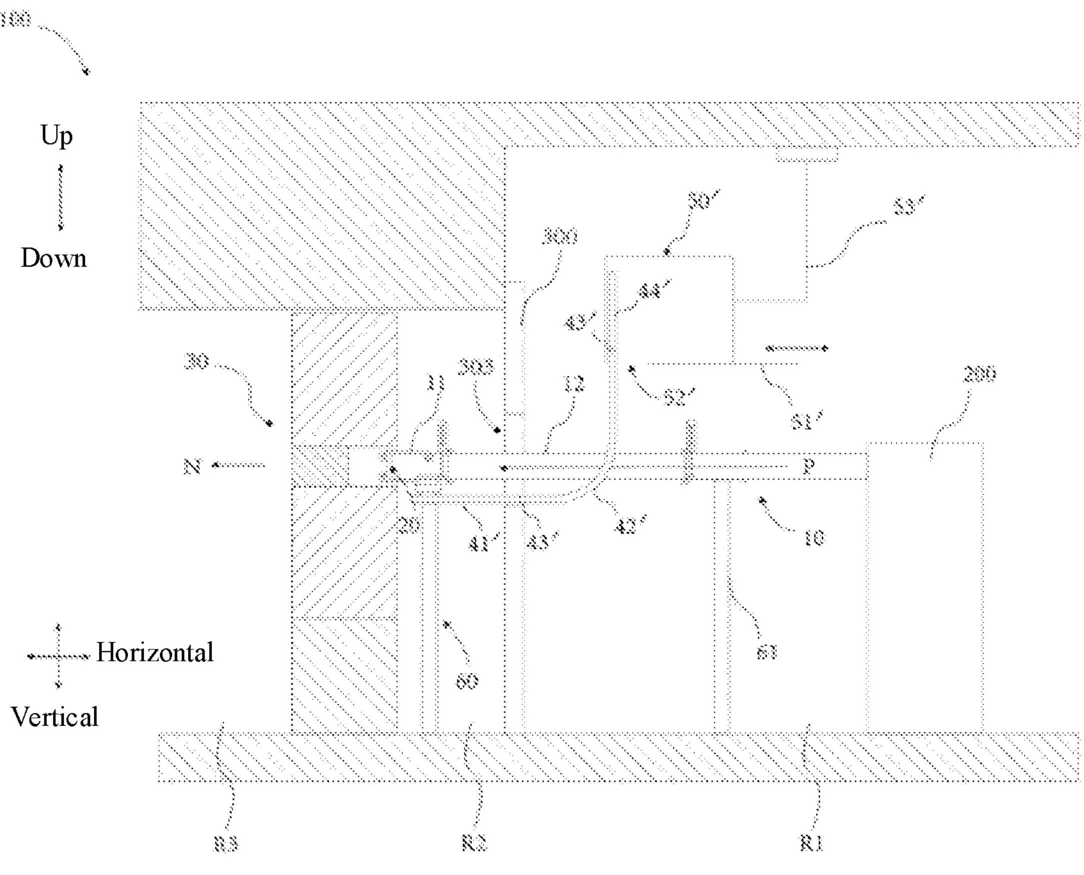
FIG. 5 is a schematic plan view of a neutron capture therapy system according to another embodiment of the disclosure.
Figure 6:
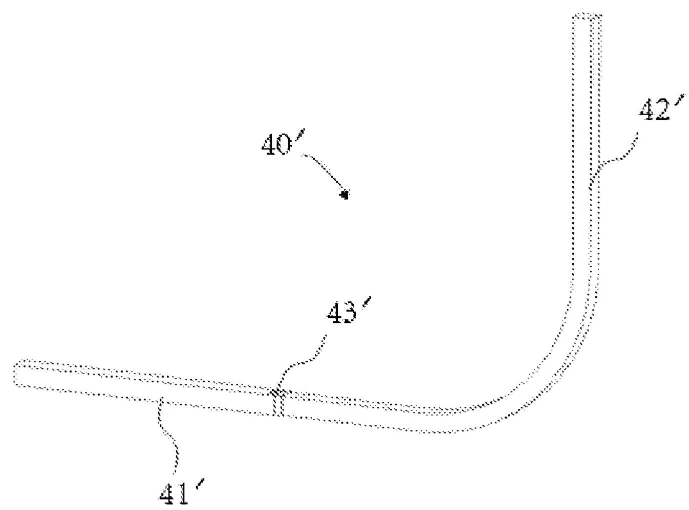
FIG. 6 is a schematic perspective view of a guidance device of a neutron capture therapy system according to another embodiment of FIG. 5.

FIG. 5 and FIG. 6 show a guidance device 40' according to another embodiment of the disclosure. The guidance device 40' includes a first rail 41' and a second rail 42', the first rail 41' substantially extends in a first direction along which the transmission device is arranged, an end of the second rail 42' is connected to the first rail 41' through a connection part 43', and the second rail 42' describes a second direction extending upward. An operable mobile mechanical structure 53' is included at top of the first space R1, and supports a radiation shielding device 50' to implement spatial positioning through 3D calculation or manual adjustment, move to a preset 3D positioning marker and is connected to the second rail 42'. An openable shielding plate 51' is arranged at bottom of the radiation shielding device 50' and is operably opened to form an accommodation opening 52'. A third rail 44' is arranged at an inner side of the radiation shielding device 50' and is operably aligned with and connected to another end of the second rail 42' through the connection part 43'. The driving device 70 (referring to FIG. 7) transmits power through the rails, moves the first transmission part 11 and the neutron generation part 20 out from the first position L1, transmits the first transmission part 11 and the neutron generation part 20 along the first rail 41', through the second rail 42', to the third rail 44' in the radiation shielding device 50, and limits and fixes the first transmission part 11 and the neutron generation part 20 to reach a second position (not shown). The second rail 42' is operably disconnected from the connection part 43' at the third rail 44', and the openable shielding plate 51' is operably closed to complete recovery operation of the first transmission part 11 and the neutron generation part 20. In an alternative embodiment, the mobile mechanical structure 53' may also be located at a different position such as a side wall of the first space R1, or the like, and the second rail may be arranged in any other directions different from extension direction of the first rail (i.e., the direction along which the transmission device is arranged) according to an actual situation.

Figure 7:
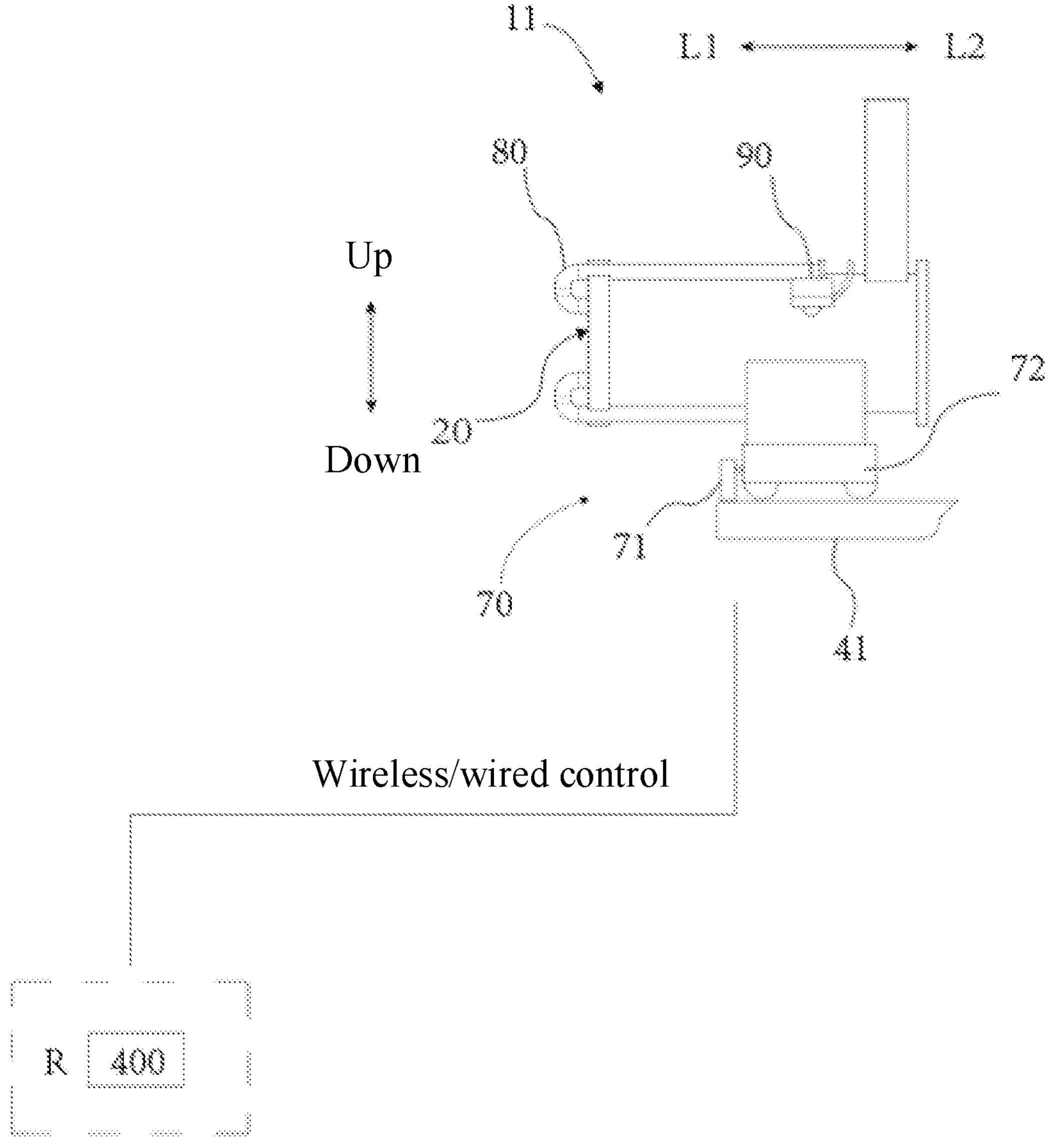
FIG. 7 shows a schematic plan view of a first transmission part of a transmission device.

FIG. 7 shows a schematic view of the first transmission part 11 of the transmission device 10, the neutron capture therapy system 100 further includes a cooling device 80 configured to cool the neutron generation part 20 and a detection device 90, besides a driving structure 70. The driving structure 70 has power and further includes a driving frame 72 carrying the first transmission part 11 and the neutron generation part 20, and a power structure 71, and the power structure 71 includes, but is not limited to, an electronic or pneumatic connection rod, a robot and structures thereof, a mechanical arm, or the like. With reference to FIG. 1 and FIG. 2, the disclosure is intended to implement unmanned operation in case that the operator leaves the radiation exposure space R2 when the neutron generation part 20 is separated from the beam shaping body 30 and radiation dose is high in the second space R2 environment. Therefore, driving of the related power structure is a remote operation implemented by the operator operating a master control panel 400 in a non-radioactive safe area R. According to the remote operation implemented by the operator operating the master control panel 400 in the non-radioactive safe area R, the power structure 71 of the driving device 70 drives the driving frame 72 carrying the first transmission part 11 and the neutron generation part 20 to move, so that the driving frame 72 drives the first transmission part 11 and the neutron generation part 20 to be separated from the beam shaping body 30 and move along the guidance device; when the first transmission part 11 and the neutron generation part 20 move to the radiation shielding device 50, a pneumatic lever of the buffer device 54 is driven by the master control panel 400 to implement safe recovery of the first transmission part 11 and the neutron generation part 20, and the master control panel 400 is operated so that the openable shielding plate 51 of the radiation shielding device 50 is closed, thereby completing recovery operation. With reference to FIG. 3, in an alternative embodiment, the shielding facility 300 and the auxiliary door on the shielding facility may also implement remote wired or wireless operation and control through the master control panel 400. The cooling device 80 includes a pipeline located at an end portion of the transmission device 10 and in planar contact with the neutron generation part 20, and two cooling pipelines arranged up and down in a direction along which the transmission device is arranged, here the two cooling pipelines arranged up and down may be partially arranged in the retarder, form a [ structure and may be communicated with an external cooling system, the neutron generation part 20 increases temperature and generates heated due to accelerated irradiation of a high energy level, and the neutron generation part 20 is efficiently cooled by a cooling medium flowing through the cooling pipelines. In the embodiment as shown, the detection device 90 may be a temperature sensor, including a detection circuit arranged along the transmission device 10 and connected to a control end, and may be configured to detect a real-time temperature of the cooling device. In an alternative embodiment, the detection device may also be a charged particle sensor, configured to detect a charged particle beam before the first transmission part 11 reacts with the neutron generation part 20; or the detection device may be a vacuum pressure sensor, configured to detect a vacuum degree of the first transmission part 11; or the detection device may be a neutron detector, configured to detect neutrons generated after occurrence of a nuclear reaction. The detection device 90 includes, but is not limited to, an electronic sensor, a proximity sensor, a capacitive sensor, a transducer, or another form of sensor. When the first transmission part 11 is located at the first position L1, the cooling pipelines are communicated with pipelines of the external cooling system, to provide a state where cooling may be implemented; and the detection circuit and circuits of the control end are in a connected state, so that real-time monitoring and data transmission and feedback may be implemented. When the first transmission part 11 is located at the second position L2, the cooling pipelines are disconnected from pipelines of the external cooling system, and the detection circuit is disconnected from connection lines of the control end. The cooling device and the partially disconnected pipelines, and the partially disconnected circuit of the detection device are arranged at the first transmission part, and move together with the first transmission part 11 to the second position to be recovered and replaced.

Figure 8:
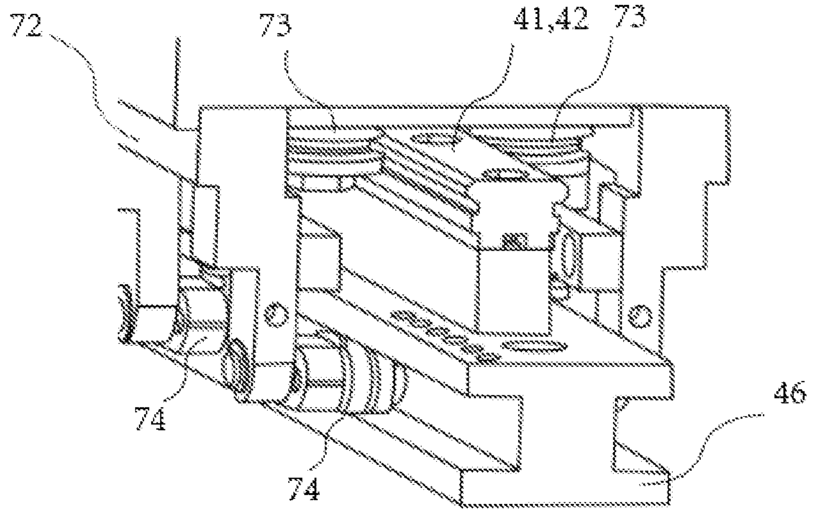
FIG. 8 is a schematic cross-sectional view of a roller set of a driving frame of a driving device of a neutron capture therapy system according to an embodiment of the disclosure.
Figure 9A:
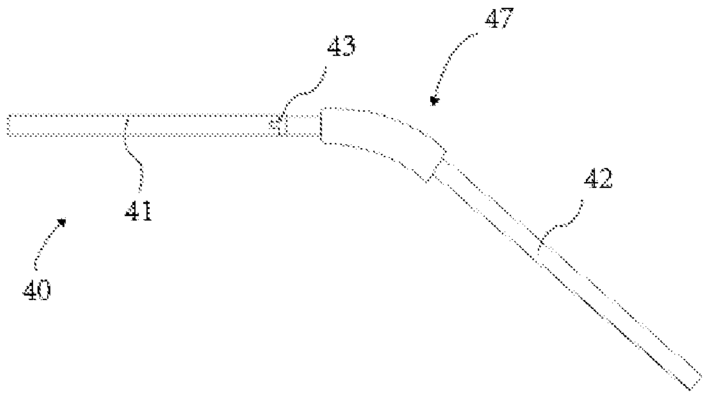
FIG. 9A and FIG. 9B are schematic usage view and schematic cross-sectional view of an anti-radiation protective cover of a guidance device of a neutron capture therapy system according to an embodiment of the disclosure, respectively.
Figure 9B:
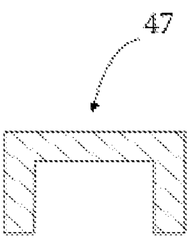

FIG. 8 shows that the driving frame 72 of the drive structure 70 includes at least one set of rollers, and in a embodiment, the driving frame 72 includes at least two sets of rollers 73, 74. With reference to FIG. 1, FIG. 4, FIG. 6 and FIG. 8, the guidance device further includes a rail base 46 and a plurality of segments of rails, the first rail 41 and the second rail 42 are laid on the rail base 46. Rolling planes of the two sets of rollers 73, 74 on the driving frame 72 are different, further, rolling directions of the two sets of rollers 73, 74 are also different, and the rolling directions of rollers in a single set of rollers are kept consistent. The roller set 73 and a rail segment above the base form a combination of the roller and a convex rail, the roller set 74 and the rail base 46 form a combination of the roller and a concave rail, the two combinations are in different modes, roll on different planes, and have rolling directions perpendicular to each other, which may reliably ensure high stability of the whole guidance operation in two dimensions, making a significant contribution to matching and adaptability of rails during subsequent switching of the rails, and even flexibility of selecting any one or two sets of rollers. In a embodiment, the rail 422 structural segment where the second rail 42 may be flexibly rotated, is provided with the rail base 46, so that during switching to the rail 422 segment, there is guidance and cooperation of the roller set 74 with the concave rail base 46 of the rail 422 segment, guidance and cooperation of the roller set 73 with the convex rail of the rail 422 segment are released, to enter the third rail 44 inside the aligned radiation shielding device 50, and the third rail 44 is in linkage alignment with the concave rail base 46 of the rail 422 segment. Considering that weights of the first transmission part 11 and the neutron generation part are large, when guidance and transmission are performed by using rollers to cooperate with a concave or convex rail in the embodiment, it is also need to comprehensively consider bearing capacity and wear resistance of the guidance device, in addition to considering metals which are not easily activated by neutrons and have a short half-life period. Therefore, selection of an aluminum alloy or aluminum-magnesium alloy material may be unable to withstand large weights of the first transmission part 11 and the neutron generation part 20, as well as abrasion of rollers on guide rails. Therefore, the guidance device further considers selection of a wear-resistant material with large rigidity, and a surface of the material is coated with a coating film configured to prevent neutron activation and capable of resisting abrasion of rollers, to reduce probability of activation of the material and prolong service life of the rail. By performing cross-sectional stress analysis on a plurality of segments of the guide rail, it may be known that load and deformation borne by the cross section of the rail at a bent segment are much larger than those borne by the rail at a linear segment. The first rail 41 and a part of the second rail 42 are rails at linear segments, and the rest part of the second rail 42 needs to form a bent segment due to change of the guiding direction, therefore the segment has high needs on rigidity and wear resistance of the material. According to the above research and analysis, in an alternative embodiment, considering that a linear guidance part located close to the beam shaping body 30 in the core reaction space R2 selects an aluminum alloy, a magnesium-aluminum alloy, and/or a material of which a surface is coated with a wear-resistant coating, a bent guidance part considers selection of stainless steel or another material with large rigidity, or considers a surface thereof to be coated with a coating film configured to prevent neutron activation and capable of resisting abrasion of rollers. Or, with reference to FIG. 9A and FIG. 9B, an anti-radiation protective cover 47 shaped to fit the guidance structure is made by using an anti-radiation material such as boron-containing PE, and/or a neutron or photon shielding material such as boron-containing resin, or the like. In an operation process of the radioactive irradiation system, the anti-radiation protective cover 47 is covered on a surface of easy-to-be-activated material of the guidance device, and when radioactive consumables are replaced, the radioactive irradiation system stops operation at this time, so that the anti-radiation protective cover 47 may be removed, and the guide rail is used normally. A plurality of different materials are selected in segments on the rail of the guidance device, so that service life of the guidance device may be greatly prolonged, and usage reliability of the guidance device may be improved.

Figure 10:
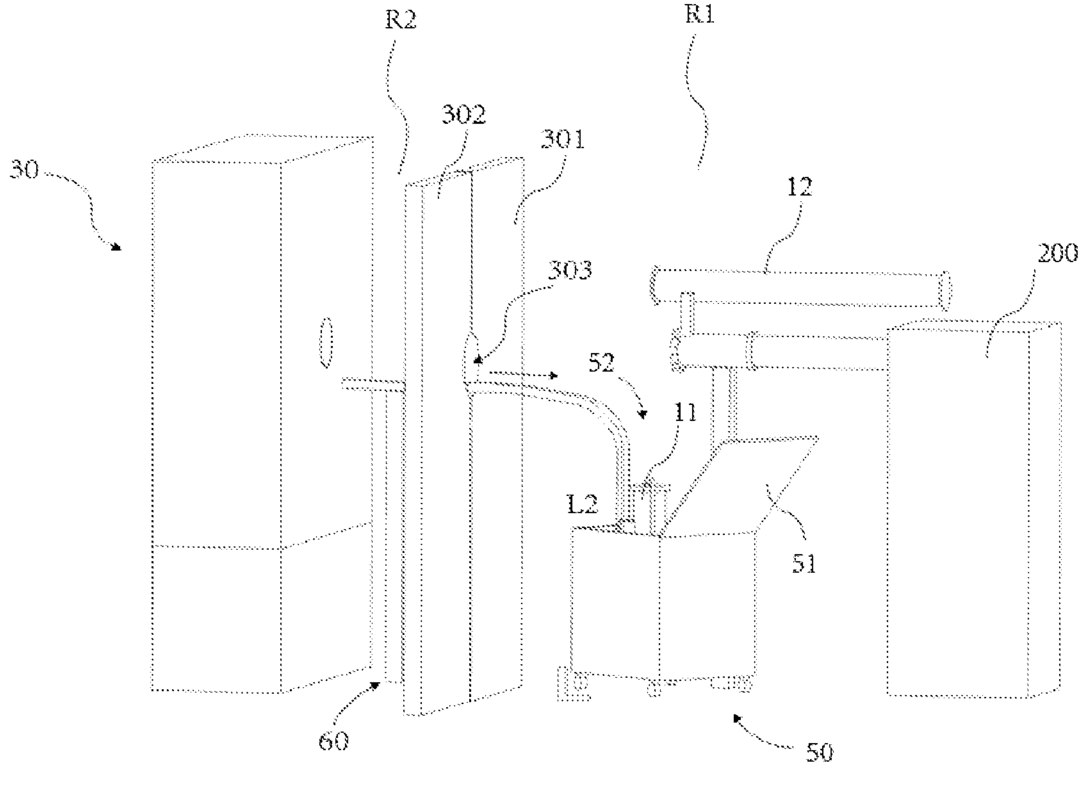
FIG. 10 is a schematic perspective view of a neutron capture therapy system according to an embodiment of the disclosure, showing a schematic view of recovering a first transmission part and a neutron generation part when a shielding facility is in a closed state.
Figure 11A:
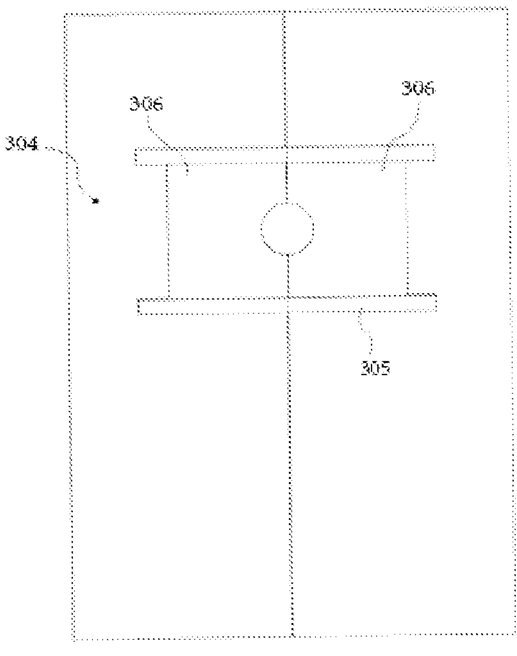
FIG. 11A to FIG. 11E are schematic views of an auxiliary door of a radiation shielding device of a neutron capture therapy system, and opening and closing states thereof according to an embodiment of the disclosure.
Figure 11B:
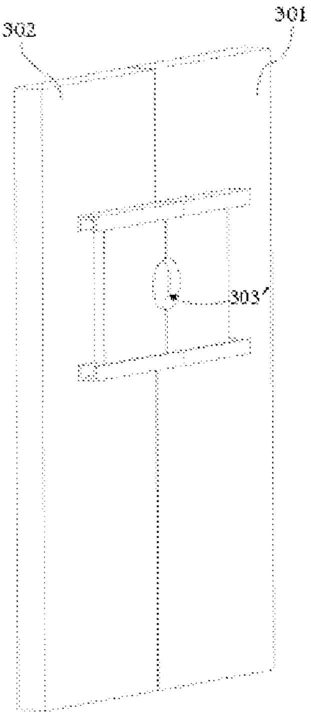
Figure 11C:
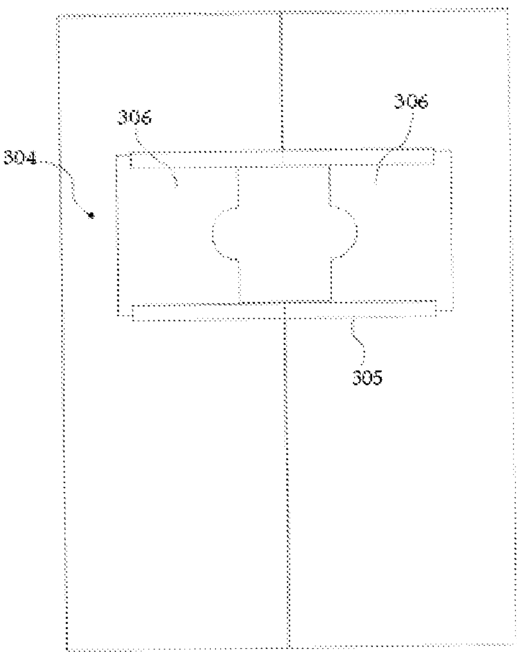
Figure 11D:
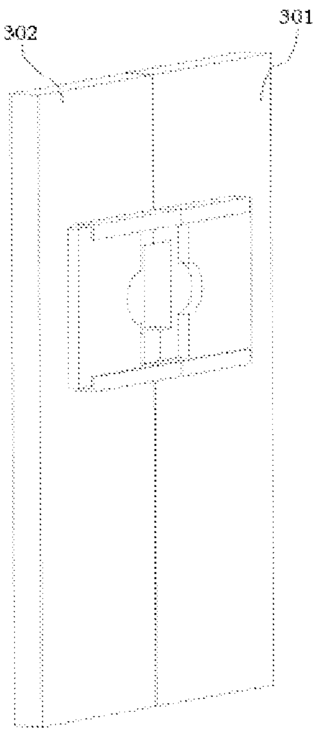
Figure 11E:
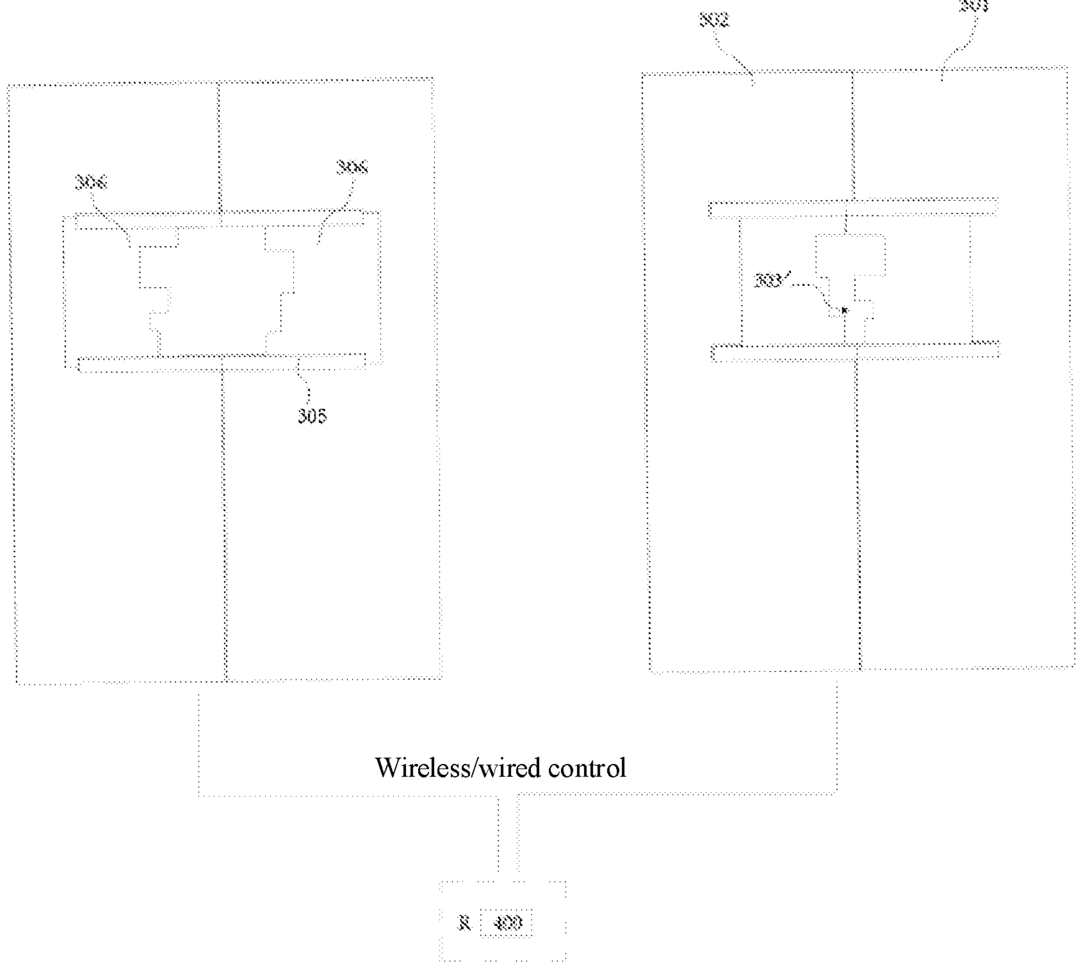

FIG. 10 is a schematic view of another embodiment of replacement of the neutron generation part, showing that the shielding facility 300 between the first space R1 and the second space R2 is in a closed state. The first space R1 is physically separated from the second space R2 when the shielding door 301 and/or the shielding door 302 are closed, and the guidance device 40 passes through the opening 303 of the shielding facility from the first space R1 into the second space R2. In that state, the operator is located in the first space R1 and may safely operate in a condition of less radiation, to recover the first transmission part and neutron generation part. As in same operations in the embodiment of FIG. 3, the operator performs preparation operations of replacement operation, completes disassembling the second transmission part 12, and checking connection and position conditions of the first rail 41, the second rail 42 and the radiation shielding device 50. In the embodiment, the operator removes and cuts off pipelines corresponding to the cooling device 80 and the detection device 90 (referring to FIG. 7) on the first transmission part 11 by using his hands or other tools to pass through the opening 303; pipelines of other pneumatic devices (not shown) may also exist on the first transmission part 11 and are removed and cut off together, and the first transmission part 11 with the neutron generation part is moved to a third position (not shown) close to the opening 303 of the shielding facility 300, and an end of the first transmission part 11 arranged with the neutron generation part is kept to be located in the second space R2. Power from the driving device (referring to FIG. 7), or a pulling force from the operator, or the like is used as a first power to be applied to the first transmission part 11, thus the first transmission part 11 with the neutron generation part generates a first movement with a small distance, and is separated and disconnected from the beam shaping body 30, and at this time, radiation value of the second space R2 is much higher than radiation value of the first space R1 due to exposure of the neutron generation part. When the neutron generation part is separated manually, the operator should be provided with appropriate protection and quickly evacuate to the safe area R. The power from the driving device 70 (referring to FIG. 7) or the pulling force from the operator is applied as a second power again, and under action of the second power, the first transmission part 11 performs a second movement with a relatively large distance on the first rail 41 in a first direction along which the transmission device 10 is arranged, to completely barrier-free pass through the opening 303 of the shielding facility 300 which is kept in a closed state, so as to move to the second rail 42 located in the first space R1, and under action of gravity or power of the rail, the first transmission part 11 continues to move to the second position L2 along the direction of the second rail 42. Shape of the opening 303 of the shielding facility 300 may be circular shape, square shape, or even irregular shape, or the like, may be adapted to cross sections of the first transmission part 11 with the neutron generation part and of the guidance device, so that it may ensure that the first transmission part 11 with the neutron generation part may smoothly pass through the shielding facility 303 and continue to move to a recovery position after auxiliary pipelines related to water, electricity and gas are disconnected, while radiation leakage is reduced to the extent. The opening 303 of the shielding facility 300 may also be provided with a shielding cover plate (not shown) made of a radiation shielding material, and during normal operation, the shielding cover plate does not shield the opening 303; and when the neutron generation part is replaced according to the above operations, the operator disassembles and disconnect the auxiliary pipelines, and moves the first transmission part 11 with the neutron generation part out, and shields the opening 303 to the extent by the movable shielding cover plate, to further reduce radiation leakage of the second space R2 to the first space R1.

With reference to FIG. 11A to FIG. 11E, the shielding facility 300 between the first space R1 and the second space R2 is in a closed state. The first space R1 is physically separated from the second space R2 when the shielding door 301 and/or the shielding door 302 are closed, and the guidance device 40 passes through the opening 303 of the shielding facility from the first space R1 into the second space R2. With reference to FIG. 10, an auxiliary door 304 is arranged at the opening 303 of the shielding facility 300, similar to the above movable shielding cover plate. The auxiliary door 304 includes a fixed part 305 and a movable part 306. The movable part 306 is divided into left and right sections which are located on fixed parts 305 fixed on the shielding doors 301 and 302 respectively. When the movable part 306 is closed, there is at least one opening 303' in the middle. In the embodiment, shape of at least one opening 303' of the auxiliary door 304 is usually fitted with shapes of the first transmission part 11, the guidance device 40 and mating pipeline structures, a vacuum valve, or the like arranged at the opening 303', to reduce radiation leakage from the opening 303' when the shielding facility 300 and the auxiliary door 304 are closed to perform irradiation therapy of the neutron beam, and the shape includes, but is not limited to, oval shape, rhombus shape, square shape, or even an irregular shape, or the like (FIG. 11A to FIG. 11E). When recovery operation of the first transmission part and the neutron generation part is performed, the auxiliary door 304 may be opened, the shielding facility 300 is kept closed, and after they are replaced by a new first transmission part and a new neutron generation part, the auxiliary door 304 is closed; or, when recovery operation of the first transmission part and the neutron generation part is performed, the shielding facility 300 is opened, and after they are replaced by a new first transmission part and a new neutron generation part, the shielding facility 300 and the auxiliary door 304 are closed. The auxiliary door 304 is made of a material with good shielding performance, and the movable member 306 of the auxiliary door 304 may be opened or closed along a path preset by the fixed member 305 when the shielding door 301 and the shielding door 302 are kept closed, such that design of such flexible, small and shape-fitted auxiliary door further reduces radiation amount during irradiation therapy of the neutron beam; furthermore, when the first transmission part or the guidance device is adjusted in shape or structure, the auxiliary door needs to be adjusted or customized, without consuming manpower and material resources to modify the heavy and bulky shielding door, while energy of moving the bulky shielding door is also saved.

In an embodiment, a method for recovering the neutron generation part includes the following operations S1 to S12.

In operation S1, the radiation shielding device is moved to the second space. In operation S2, the first transmission part is kept in a vacuum state, and a second transmission part between the first transmission part and the third transmission part is removed.

In operation S3, auxiliary pipelines related to water, electricity and gas, such as the cooling pipeline and the detection circuit, are removed.

In operation S4, the radiation shielding device is pushed to position of a ground positioning member, to stop, lock and fix the radiation shielding device, and the openable member of the radiation shielding device is opened at this time.

In operation S5, the anti-radiation protective cover on the guidance device is removed, and the second guidance part is connected to and aligned with the third guidance part in the radiation shielding device.

In operation S6, the operator exits from the second space to a safe area.

In operation S7, a driving device switch on the master control panel is triggered, to drive the power structure to push out the driving frame where the first transmission part and the neutron generation part are installed, and move the driving frame to the radiation shielding device along the guidance device.

In operation S8, a control switch, for the openable member of the radiation shielding device, on the master control panel is triggered, so that the openable member is closed to prevent radiation leakage.

In operation S9, the anti-radiation protective cover is covered on the guidance device.

In operation S10, the ground positioning member is unlocked, and the radiation shielding device is pushed out of the second space.

In operation S11, a new neutron generation part is installed, to complete connection of the first transmission part, the second transmission part and the third transmission part.

In operation S12, auxiliary pipelines related to water, electricity and gas, such as the cooling pipeline and the detection circuit, are connected, and the transmission device is debugged.

The neutron capture therapy system disclosed in the disclosure is not limited to contents described in the above embodiments and structures represented by the drawings, for example, both embodiments of FIG. 5 and FIG. 6 are applicable to operations of replacing the neutron generation part in a state where the shielding facility is opened or closed; the structure detachably connected to the transmission device may also be fixed by a quick clamping structure, or may be a structure fixed by bolts and nuts, and a part of the transmission device is configured as a telescopic corrugated pipe, a folding pipe, a telescopic pipe, or the like. Furthermore, manners of driving the first transmission part to be disconnected from the beam shaping body and move, controlling the radiation shielding device to move to a preset position, opening and closing the openable shielding member, and docking and separating rails are not limited to movement caused by hands or gravity, and may also be an operator's short-range and remote operations and automatic control. Based on the disclosure, apparent variations, replacements or amendments made to materials, shapes and positions of components therein, fall within the scope of protection of the disclosure.

The neutron capture therapy system disclosed by the disclosure is not limited to contents described in the above mentioned embodiments and structures represented by accompanying drawings. Apparent changes, substitutions or modifications made on materials, shapes and positions of components therein based on the disclosure shall fall within the protection scope of the disclosure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and might be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A neutron capture therapy system, characterized in that the neutron capture therapy system comprises an accelerator configured to generate a charged particle beam, a transmission device configured to transmit the charged particle beam and comprising at least a first transmission part and a second transmission part, a neutron generation part configured to generate a neutron beam by reacting with the charged particle beam, a beam shaping body configured to perform spectrum adjustment on the neutron beam, and a guidance device, wherein the first transmission part is detachably connected to the second transmission part and comprises a first position and a second position, the neutron generation part is arranged on the first transmission part, and the guidance device is capable of guiding the first transmission part to move from the first position to the second position, and wherein when the first transmission part is located at the first position, the neutron generation part is accommodated in the beam shaping body and is capable of reacting with the charged particle beam to generate neutrons; and when the first transmission part is located at the second position, the neutron generation part is separated from the beam shaping body.

2. The neutron capture therapy system of claim 1, wherein the guidance device comprises a first guidance part and a second guidance part, of which guiding directions are different from each other.

3. The neutron capture therapy system of claim 2, wherein in a plane where the first guidance part is located parallel to the ground, a projection of a connection line between a first end and a second end of the second guidance part forms a first angle with the first guidance part; and in a plane where the first guidance part is located perpendicular to the ground, a projection of the connection line between the first end and the second end of the second guidance part forms a second angle with the first guidance part.

4. The neutron capture therapy system of claim 2, wherein the second guidance part comprises at least two segments of guide rails, one of which is a fixed rail detachably connected to the first guidance part, and the other of which is movable rail rotatably connected to the fixed rail.

5. The neutron capture therapy system of claim 4, wherein the movable rail is connected to the fixed rail through a hinge structure and have two positions, and when the movable rail is located at a first position, the movable rail and the fixed rail keep a normal guidance state together; and when the movable rail is stressed and located at a second position, the movable rail moves at a certain angle relative to the fixed rail, and automatically return to the first position.

6. The neutron capture therapy system of claim 1, further comprising a driving device which is capable of moving the first transmission part arranged with the neutron generation part out from the first position, and comprises a driving frame carrying the first transmission part and the neutron generation part and a power structure providing a driving force.

7. The neutron capture therapy system of claim 6, the driving frame of the driving device comprises at least one set of roller structures.

8. The neutron capture therapy system of claim 2, further comprising a movable radiation shielding device configured to accommodate the first transmission part and the neutron generation part guided by the guidance device, and the guidance device further comprising a third guidance part which is fixedly accommodated in the movable radiation shielding device.

9. The neutron capture therapy system of claim 8, wherein the radiation shielding device is made of a radiation shielding material and comprises an openable member, the radiation shielding device forms an accommodation opening when the openable member is opened, the first transmission part of the transmission device enters the radiation shielding device from the accommodation opening, and the neutron generation part enters the radiation shielding device from the accommodation opening; and the radiation shielding device forms a closed shielding space when the openable member is closed, to prevent radiation leakage of the neutron generation part.

10. The neutron capture therapy system of claim 8, wherein the movable radiation shielding device further comprises a buffer device, to avoid damage to at least the first transmission part or the radiation shielding device.

11. The neutron capture therapy system of claim 2, wherein the second guidance part is coated with an anti-radiation film, and/or a removable anti-radiation protective cover which is added to the surface of the second guidance part.

12. The neutron capture therapy system of claim 1, the neutron capture therapy system further comprising a detection device with a detection circuit, and wherein:

when the first transmission part is located at the first position, the detection device is in an on state to perform detection operation; and when the first transmission part is located at the second position, the detection circuit is in an off state.

13. A method for recovering the neutron generation part of a neutron capture therapy system, the neutron capture therapy system comprises an accelerator configured to generate a charged particle beam, a transmission device configured to transmit the charged particle beam and comprising at least a first transmission part and a second transmission part, a neutron generation part configured to generate a neutron beam by reacting with the charged particle beam, a beam shaping body configured to perform spectrum adjustment on the neutron beam, and a guidance device, the first transmission part is detachably connected to the second transmission part and comprises a first position and a second position, characterized in that the method for recovering the neutron generation part comprises:

splitting the first transmission part and the second transmission part apart; and applying a first power to the first transmission part arranged with the neutron generation part, to separate the first transmission part from the beam shaping body along the guidance device.

14. The method for recovering the neutron generation part of claim 13, wherein the guidance device comprises a first guidance part and a second guidance part, characterized in that the method for recovering the neutron generation part comprises:

driving the first transmission part arranged with the neutron generation part along the first guidance part to the second guidance part second guidance part which guiding direction is different from the first guidance part.

15. The method for recovering the neutron generation part of claim 13, wherein the neutron capture therapy system further comprises a radiation shielding device configured to accommodate the neutron generation part after recovery, characterized in that the method for recovering the neutron generation part comprises:

driving the first transmission part to enter the radiation shielding device earlier than the neutron generation part along the guidance device.

16. The method for recovering the neutron generation part of claim 13, wherein the neutron capture therapy system further comprising an auxiliary pipeline connected to the neutron generation part or the first transmission part, characterized in that the method for recovering the neutron generation part comprises:

disconnecting the auxiliary pipeline from the neutron generation part; and applying a second power to the first transmission part arranged with the neutron generation part, to move the first transmission part along the guidance device, until to a recovery position.

17. The method for recovering the neutron generation part of claim 14, wherein the neutron capture therapy system further comprises a shielding facility provided with an opening, and the first transmission part passes through the opening in a state where the shielding facility is kept closed.

18. The method for recovering the neutron generation part of claim 16, wherein the shielding facility is provided with an auxiliary door, the auxiliary door at least partially shields the opening of the shielding facility and has an opening fitted with contours of the first transmission part, the guidance device and the auxiliary pipeline arranged at the opening of the shielding facility when the auxiliary door is closed, and the method for recovering the neutron generation part is carried out through the opening in a state where the shielding facility is kept closed and the auxiliary door is kept open.

* * * * *